(12) United States Patent
Prachar (10) Patent No.: US 10,750,951 B1
(45) Date of Patent: Aug. 25, 2020

(54) CORE TEMPERATURE MEASUREMENT USING ASYMMETRIC SENSORS

(71) Applicant: Verily Life Sciences LLC, Mountain View, CA (US)

(72) Inventor: Timothy John Prachar, Menlo Park, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 285 days.

(21) Appl. No.: 15/053,607

(22) Filed: Feb. 25, 2016

(51) Int. Cl.
*A61B 5/01* (2006.01)
*G01K 1/16* (2006.01)
(Continued)

(52) U.S. Cl.
CPC .............. *A61B 5/01* (2013.01); *A61B 5/441* (2013.01); *A61B 5/6804* (2013.01); *G01K 1/16* (2013.01);
(Continued)

(58) Field of Classification Search
CPC ........ G01K 13/002; G01K 1/16; G01K 1/165; G01K 1/18; A61B 5/01; A61B 5/441;
(Continued)

(56) References Cited

U.S. PATENT DOCUMENTS 6,909,271 B2 * 6/2005 Sloneker .............. G01K 7/021
324/117 R
8,292,495 B2 * 10/2012 Bieberich ............ G01K 13/002
374/1
(Continued)

FOREIGN PATENT DOCUMENTS

FR 2966927 A1 * 5/2012 ............... A61B 5/01
JP S61120026 A 6/1986
(Continued)

OTHER PUBLICATIONS

Kitamura et al., "Development of a New Method for the Noninvasive Measurement of Deep Body Tempeature Without a Heater," Med Eng Phys. Jan. 2010;32(1):1-6. doi: 10.1016/j.medengphy. 2009-09-004. Epub Nov. 10, 2009. Abstract Only, 1 page.
(Continued)

*Primary Examiner* — David J. McCrosky
(74) *Attorney, Agent, or Firm* — McDonnell Boehnen Hulbert & Berghoff LLP (57) ABSTRACT

A temperature measurement system determines a body temperature. The system includes a first temperature sensor; a first insulation material thermally coupled to the first temperature sensor with a first thermal resistance; a second temperature sensor spaced from the first temperature sensor; a second insulation material thermally coupled to the second temperature sensor with a second thermal resistance that is different from the first thermal resistance; an isothermal plate thermally coupled to the first insulation material and the second insulation material; and an isothermal plate temperature sensor. Heat conduction occurs along a first heat conduction path from the body, through the first insulation material, and to the isothermal plate, and the first temperature sensor measures a first temperature. Heat conduction occurs along a second heat conduction path from the body, through the second insulation material, and to the isothermal plate, and the second temperature sensor measures a second temperature.

19 Claims, 6 Drawing Sheets

(51) Int. Cl.
*G01K 13/00* (2006.01)
*A61B 5/00* (2006.01)

(52) U.S. Cl.
CPC .... *G01K 13/002* (2013.01); *A61B 2560/0214* (2013.01); *A61B 2562/0271* (2013.01); *A61B 2562/04* (2013.01); *A61B 2562/18* (2013.01)

(58) Field of Classification Search
CPC .............. A61B 5/6804; A61B 2562/18; A61B 2560/0214; A61B 2562/0271; A61B 2562/04
See application file for complete search history.

(56) References Cited

U.S. PATENT DOCUMENTS

| | | | | |
|---|---|---|---|---|
| 8,292,502 B2 * | 10/2012 | Bieberich | ............ | G01K 13/002 374/163 |
| 2007/0295713 A1 * | 12/2007 | Carlton-Foss | ........... | A61B 5/01 219/497 |
| 2011/0249699 A1 | 10/2011 | Bieberich et al. | | |
| 2013/0317388 A1 * | 11/2013 | Bieberich | .............. | G01K 1/165 600/549 |
| 2016/0066839 A1 * | 3/2016 | Ikeda | ................... | A61B 5/4866 600/549 |

FOREIGN PATENT DOCUMENTS

| | | | | |
|---|---|---|---|---|
| JP | S61120027 A | | 6/1986 | |
| JP | S6358223 A | | 3/1988 | |
| JP | 2006308538 A | * | 11/2006 | ............. G01K 1/165 |
| JP | 2007212407 A | * | 8/2007 | |
| JP | 2012132818 A | * | 7/2012 | |
| WO | WO 2011012386 A1 | * | 2/2011 | |
| WO | WO 2014157138 A1 | * | 10/2014 | ........... G01K 13/002 |

OTHER PUBLICATIONS

Benson et al, "Design of a Variable-Conductance Vacuum Insulation," National Renewable Energy Laboratory, NREL/TP-452-5814—UC Category: 270—DE94000270, Jan. 1994, 8 pages.

* cited by examiner

CORE TEMPERATURE MEASUREMENT USING ASYMMETRIC SENSORS

BACKGROUND

Unless otherwise indicated herein, the materials described in this section are not prior art to the claims in this application and are not admitted to be prior art by inclusion in this section.

Assessment of a person's health often involves measuring the person's core body temperature. Invasive approaches for determining core body temperature may involve taking measurements within the pulmonary artery, esophagus, rectum, or bladder. Non-invasive approaches may involve taking measurements in the mouth, under the armpit, in the ear canal, or at the temples of the head. Non-invasive approaches are generally more convenient than invasive approaches, especially when frequent temperature measurements are taken. It may be more difficult, however, to obtain accurate measurements of the core body temperature with non-invasive approaches.

SUMMARY

Non-invasive approaches may involve measuring temperature at the surface of the skin. A temperature measurement at the skin surface, however, may not accurately reflect the core body temperature below the skin, because the thermal resistance of the skin prevents effective conduction of heat from the core to the skin surface. To determine core body temperature accurately from temperature measurements taken at the skin surface, aspects of the present disclosure account for the thermal resistance of the skin on the temperature measurements.

In an example embodiment, a temperature measurement system for determining a body temperature of a person includes a first temperature sensor. The system includes a first insulation material thermally coupled to the first temperature sensor and having a first thermal resistance. The system includes a second temperature sensor spaced apart from the first temperature sensor. The system includes a second insulation material thermally coupled to the second temperature sensor and having a second thermal resistance that is different from the first thermal resistance. The system includes an isothermal plate thermally coupled to the first insulation material and the second insulation material. The system includes an isothermal plate temperature sensor thermally coupled to the isothermal plate. A first heat conduction occurs along a first heat conduction path from a body of a person, through the first insulation material, and to the isothermal plate. The first temperature sensor correspondingly measures a first temperature. A second heat conduction occurs along a second heat conduction path from the body of the person, through the second insulation material, and to the isothermal plate. The second temperature sensor correspondingly measures a second temperature.

In another example embodiment, a method for determining a body temperature of a person includes positioning a measurement device on a skin surface of a person. The measurement device includes a first temperature sensor. The measurement device includes a first insulation material thermally coupled to the first temperature sensor and having a first thermal resistance. The measurement device includes a second temperature sensor spaced apart from the first temperature sensor. The measurement device includes a second insulation material thermally coupled to the second temperature sensor and having a second thermal resistance that is different from the first thermal resistance. The measurement device includes an isothermal plate thermally coupled to the first insulation material and the second insulation material. The measurement device includes an isothermal plate temperature sensor thermally coupled to the isothermal plate. A first heat conduction occurs along a first heat conduction path from the body of the person, through the first insulation material, and to the isothermal plate. A second heat conduction occurs along a second heat conduction path from the body of the person, through the second insulation material, and to the isothermal plate. The method includes measuring, with the first temperature sensor, a first temperature. The method includes measuring, with the second temperature sensor, a second temperature. The method includes measuring, with the isothermal plate temperature sensor, an isothermal plate temperature of the isothermal plate. The method includes calculating, with a controller, a body temperature of the body of the person by evaluating the first heat conduction path and the second heat conduction path based on the first temperature, the second temperature, the isothermal plate temperature, the first thermal resistance, and the second thermal resistance.

In yet another embodiment, a temperature measurement system for determining a body temperature of a person includes a plurality of skin surface temperature sensors. The system includes a plurality of insulation materials thermally coupled respectively to the plurality of skin surface temperature sensors. The insulation materials have different respective thermal resistances. The system includes an isothermal plate thermally coupled to the plurality of insulation materials. The system includes an isothermal plate temperature sensor in thermal contact with the isothermal plate. The system includes a controller electrically coupled to the plurality of skin surface temperature sensors and the isothermal plate temperature sensor to determine respective skin surface temperatures and the isothermal plate temperature. The controller calculates a body temperature from a body of the person by evaluating heat conduction from the body of the person, through the plurality of insulation materials, and to the isothermal plate, wherein the heat conduction is evaluated according to the skin surface temperatures and the isothermal plate temperature.

These as well as other aspects, advantages, and alternatives, will become apparent to those of ordinary skill in the art by reading the following detailed description, with reference where appropriate to the accompanying drawings.

While the invention is susceptible to various modifications and alternative forms, specific embodiments have been shown by way of example in the Figures and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims. It should be understood that other embodiments may include more or less of each element shown in a given Figure. Further, some of the illustrated elements may be combined or omitted. Yet further, an example embodiment may include elements that are not illustrated in the Figures.

DETAILED DESCRIPTION

The following detailed description describes various features and functions of the disclosed systems and methods with reference to the accompanying figures. In the Figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. OVERVIEW

Assessment of a person's health often involves measuring the person's core body temperature. Invasive approaches for determining core body temperature may involve taking measurements within the pulmonary artery, esophagus, rectum, or bladder. Non-invasive approaches may involve taking measurements in the mouth, under the armpit, in the ear canal, or at the temples of the head. Non-invasive approaches are generally more convenient than invasive approaches, especially when frequent temperature measurements are taken. It may be more difficult, however, to obtain accurate measurements of the core body temperature with non-invasive approaches.

Non-invasive approaches may involve measuring temperature at the surface of the skin. A temperature measurement at the skin surface, however, may not accurately reflect the core body temperature below the skin, because the thermal resistance of the skin prevents effective conduction of heat from the core to the skin surface. Additionally, the ambient air may affect the temperature measurement at the skin surface. Indeed, the temperature at the skin surface may be several degrees (° C.) lower than the core body temperature due to the thermal resistance of the skin and the temperature effects of the ambient air.

Therefore, to measure the core body temperature accurately from temperature measurements taken non-invasively at the skin surface, example embodiments account for the effect of the thermal resistance of the skin on the temperature measurements. To determine the thermal resistance of the skin, the example embodiments evaluate how heat from the core of the body is conducted through the skin in response to varying thermal resistance loads. Additionally, the example embodiments reduce the effect of the ambient air on the measurements taken at the skin surface.

II. EXAMPLE EMBODIMENTS FOR MEASURING BODY TEMPERATURE

FIGS. 1-5 illustrate an example temperature measurement device 100. The measurement device 100 is positioned on a surface 30 of a person's skin 20, where the measurement device 100 can non-invasively and accurately determine a temperature $T_{Core}$ of the person's core 10 under the skin 20.

Figure 2:
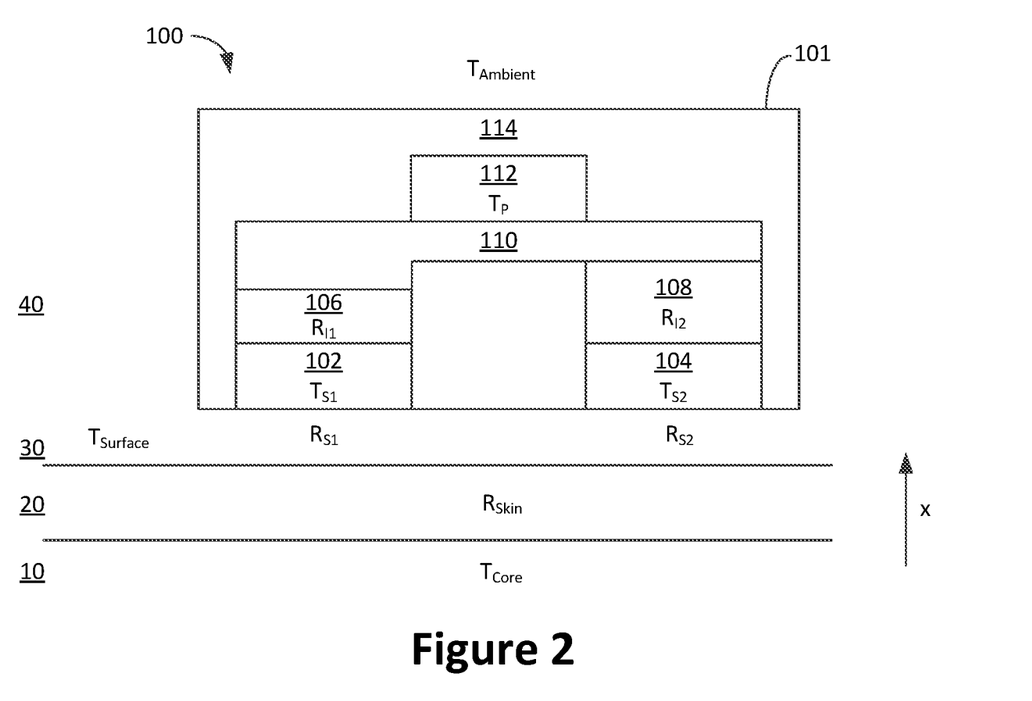
FIG. 2 illustrates data associated with the example measurement device of FIG. 1, according to aspects of the present disclosure.

As FIG. 2 illustrates, the skin 20 has a thermal resistance $R_{Skin}$. A measurement of a temperature $T_{Surface}$ at the skin surface 30 may not accurately reflect the temperature $T_{Core}$ at the core 10, because the thermal resistance $R_{Skin}$ of the intervening layer of skin 20 prevents effective conduction of heat from the core 10 to the skin surface 30. Additionally, the ambient air 40 at a temperature $T_{Ambient}$ may affect the temperature $T_{Surface}$. The temperature $T_{Surface}$ may be several degrees (° C.) lower than the core body temperature $T_{Core}$ due to the thermal resistance $R_{Skin}$ and the temperature effects of the ambient air 40.

Therefore, to measure the core body temperature $T_{Core}$ accurately, the measurement device 100 accounts for the effect of the thermal resistance $R_{Skin}$ of the skin 20 on temperature measurements taken at the skin surface 30. Additionally, the measurement device 100 reduces the effect of the ambient air 40 on the measurements taken by the measurement device 100.

Figure 1:
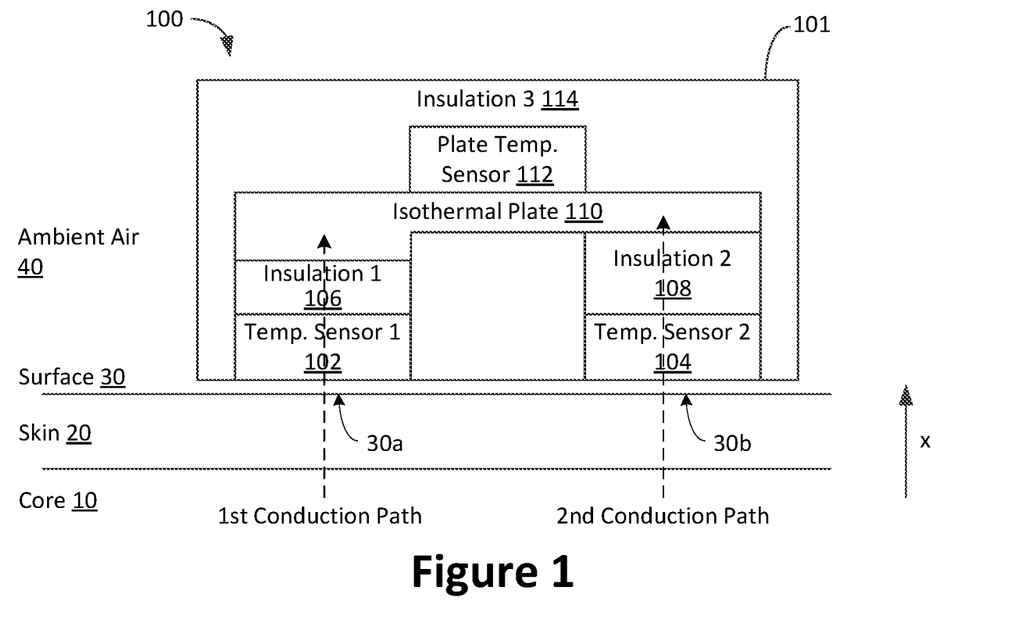
FIG. 1 illustrates an example measurement device that determines core body temperature, according to aspects of the present disclosure.

As shown in FIG. 1, the measurement device 100 includes a first temperature sensor 102 and a second temperature sensor 104. The first temperature sensor 102 and the second temperature sensor 104 may include thermistors, whose temperature-dependent resistance can be electrically determined to measure temperature. The first temperature sensor 102 is positioned to measure a temperature $T_{S1}$ at a first area 30a of the skin surface 30. The second temperature sensor 104 is positioned to measure a temperature $T_{S2}$ at a second area 30b of the skin surface 30, where the second area 30b is spaced a distance from the first area 30a. In general, the first temperature sensor 102 and the second temperature sensor 104 are spaced to allow the skin 20 to equilibrate for measurement of the temperatures at the skin surface areas 30a, b as described herein.

As illustrated in FIG. 2, the first temperature sensor 102 is associated with a thermal resistance $R_{S1}$. Similarly, the second temperature sensor 104 is associated with a thermal resistance $R_{S2}$. As the first temperature sensor 102 and the second temperature sensor 104 may be similar devices applied to the skin surface 30 in a similar manner, the thermal resistances $R_{S1}$ and $R_{S2}$ may be substantially equal.

The measurement device 100 also includes a first insulation material 106 and a second insulation material 108. As shown, the first insulation material 106 forms a layer above the first temperature sensor 102, and the second insulation material 108 forms a layer above the second temperature sensor 104. The first temperature sensor 102 is disposed between the first skin surface area 30a and the first insulation material 106. The second temperature sensor 104 is disposed between the second skin surface area 30b and the second insulation material 108. The first insulation material 106 is thermally coupled to the first skin surface area 30a via the first temperature sensor 102. The second insulation material 108 is thermally coupled to the second skin surface area 30b via the second temperature sensor 104.

As further illustrated in FIG. 2, the first insulation material 106 is produced to have a designed thermal resistance $R_{I1}$. The second insulation material 108 is produced to have a designed thermal resistance $R_{I2}$. The thermal resistance $R_{I2}$ for the second insulation material 108, however, is different from the thermal resistance $R_{I1}$ for the first insulation material 106. Due to the difference in thermal resistances $R_{I1}$ and $R_{I2}$, the measurement device 100 may be considered to be an asymmetric sensor.

In addition, the measurement device 100 includes an isothermal plate 110 that is thermally coupled to the first insulation material 106 and the second insulation material 108. The first insulation material 106 is disposed between the first temperature sensor 102 and the isothermal plate 110. Similarly, the second insulation material 108 is disposed between the second temperature sensor 106 and the isothermal plate 110. Due to its isothermal properties, the plate 110 has a substantially uniform temperature $T_P$ at steady state. The measurement device 100 also includes a plate temperature sensor 112 to measure a temperature $T_P$ for the isothermal plate 110. The plate temperature sensor 112 may also include a thermistor, whose temperature-dependent resistance can be electrically determined to measure temperature.

As shown, on the bottom surface, the first insulation material 106 has a temperature $T_{S1}$ as measured by the first temperature sensor 102, and on the top surface, the first insulation material 106 has a temperature $T_P$ as measured by the plate temperature sensor 112. Meanwhile, on the bottom surface, the second insulation material 108 has a temperature $T_{S2}$ as measured by the second temperature sensor 104, and on the top surface, the second insulation material 106 also has a temperature $T_P$ as measured by the plate temperature sensor 112.

The measurement device 100 includes a housing 101 that contains the first temperature sensor 102, the second temperature sensor 104, the first insulation 106, the second insulation 108, the isothermal plate 110, and the plate temperature sensor 112. The measurement device 100 also includes a third insulation material 114 that effectively insulates these components from heat transfer with the ambient air 40. In particular, the third insulation material 114 reduces the effect of the ambient air 40 on the temperature measurements taken by the first temperature sensor 102 and the second temperature sensor 104 at the skin surface 30.

In operation, the measurement device 100 is placed on the skin surface 30. The first temperature sensor 102 and the second temperature sensor 104 are applied to the skin surface 30 with enough pressure to help ensure full and consistent contact. Such contact helps to prevent air gaps which can introduce additional undesired thermal resistance at the skin surface 30. Moreover, such contact helps to insulate the first temperature sensor 102 and the second temperature sensor 104 from undesired heat exchange with the ambient air 40 and to ensure that substantially all heat exchange occurs through the skin 20.

Once the measurement device 100 is placed on the skin surface 30, heat from the core 10 is conducted along a first conduction path and a second conduction path in the x-direction as shown in FIG. 1. The first heat conduction path includes: (i) the skin 20 at the area 30a, (ii) the first temperature sensor 102, (iii) the first insulation material 106, and (iv) the isothermal plate 110. The second heat conduction path includes: (i) the skin 20 at the area 30b, (ii) the second temperature sensor 104, (iii) the second insulation material 108, and (iv) the isothermal plate 110.

After a period of time, the heat conduction from the core 10 into the measurement device 100 reaches steady state. In particular, temperatures $T_{S1}$, $T_{S2}$, and $T_P$ remain unchanged when the system reaches steady state. The temperatures $T_{S1}$, $T_{S2}$, and $T_P$ measured by the respective temperature sensors 102, 104, 112 may be monitored to determine when steady state has been achieved.

Once steady state has been achieved, the measurement device 100 can determine the core body temperature $T_{Core}$. The heat conduction into the measurement device 100 follows Fourier's Law, which can be generally expressed as:

$$q_x = \Delta T/R \quad (1)$$

where $q_x$ is the heat transfer rate along the x-direction, $\Delta T$ is the difference in temperature between two points, and R is the thermal resistance between the two points.

For heat conduction from the core 10 to the isothermal plate 110 along the first conduction path, $\Delta T$ is given by the difference between the temperatures $T_{Core}$ and $T_P$, and R is given by the sum of the thermal resistances from the core 10 to the isothermal plate 110, i.e., the thermal resistance $R_{Skin}$ from the skin 20, the thermal resistance $R_{S1}$ at the first temperature sensor 102, and the thermal resistance $R_{I1}$ from the first insulation material 106. Thus, $$q_x(\text{core to plate,1st path}) = (T_{Core} - T_P)/(R_{Skin} + R_{S1} + R_{I1}) \quad (2)$$

For heat conduction from the first temperature sensor 102 to the isothermal plate 110 along the first conduction path, $\Delta T$ is given by the different between the temperatures $T_{S1}$ and $T_P$, and R is given by the sum of the thermal resistances from the first temperature sensor 102 to the isothermal plate 110, i.e., the thermal resistance $R_{I1}$ from the first insulation material 106. Thus, $$q_x(\text{sensor to plate,1st path}) = (T_{S1} - T_P)/R_{I1} \quad (3)$$

At steady state, the heat transfer rate from the core 10 to the isothermal plate 110 is the same as the heat transfer rate from the first temperature sensor 102 to the isothermal plate 110. Thus, $$q_x(\text{core to plate,1st path}) = q_x(\text{sensor to plate,1st path}) \quad (4)$$

or, $$(T_{Core} - T_P)/(R_{Skin} + R_{S1} + R_{I1}) = (T_{S1} - T_P)/R_{I1} \quad (5)$$

or, $$T_{Core} = [((R_{Skin} + R_{S1} + R_{I1})/R_{I1}) * (T_{S1} - T_P)] + T_P \quad (6)$$

Similar calculations can be made for the second conduction path to find:

$$T_{Core} = [((R_{Skin} + R_{S2} + R_{I2})/R_{I2}) * (T_{S2} - T_P)] + T_P \quad (7)$$

It can be assumed that the temperature $T_{Core}$ at the core 10 and the thermal resistance $R_{Skin}$ of the skin 20 are the same for the first conduction path and the second conduction path. As such, equations (6) and (7) may be combined as a system of two equations.

As described above, the temperatures $T_{S1}$, $T_{S2}$, and $T_P$ can be measured with the first temperature sensor 102, the second temperature sensor 104, and the plate temperature sensor 112, respectively. Additionally, the thermal resistances $R_{I1}$ and $R_{I2}$ are known from the design of the first insulation material 106 and the second insulation material 108, respectively. Meanwhile, the following values are unknown: the core body temperature $T_{Core}$, the thermal resistance $R_{Skin}$ of the skin 20, the thermal resistance $R_{S1}$ associated with the first insulation material 106, and the thermal resistance $R_{S2}$ associated with the second insulation material 108.

As also described above, the thermal resistances $R_{S1}$ and $R_{S2}$ may be substantially equal, because the first temperature sensor 102 and the second temperature sensor 104 may be similar devices applied to the skin surface 30 in a similar manner. Assuming $R_{S1}=R_{S2}$, $$T_{Core}=[((R_{Skin}+R_{S1}+R_{I1})/R_{I1})*(T_{S1}-T_P)]+T_P \quad (8)$$

$$T_{Core}=[((R_{Skin}+R_{S1}+R_{I2})/R_{I2})*(T_{S2}-T_P)]+T \quad (9)$$

When the term $(R_{Skin}+R_{Sensor1})$ in equations (8) and (9) is expressed as a single thermal resistance $R_{Skin+S1}$:

$$T_{Core}=[((R_{Skin+S1}+R_{I1})/R_{I1})*(T_{S1}-T_P)]+T_P \quad (10)$$

$$T_{Core}=[((R_{Skin+S1}+R_{I2})/R_{I2})*(T_{S2}-T_P)]+T_P \quad (11)$$

Thus, the two equations (8) and (9) can be solved for the two unknown values $R_{Skin+S1}$ and $T_{Core}$.

Figure 3:
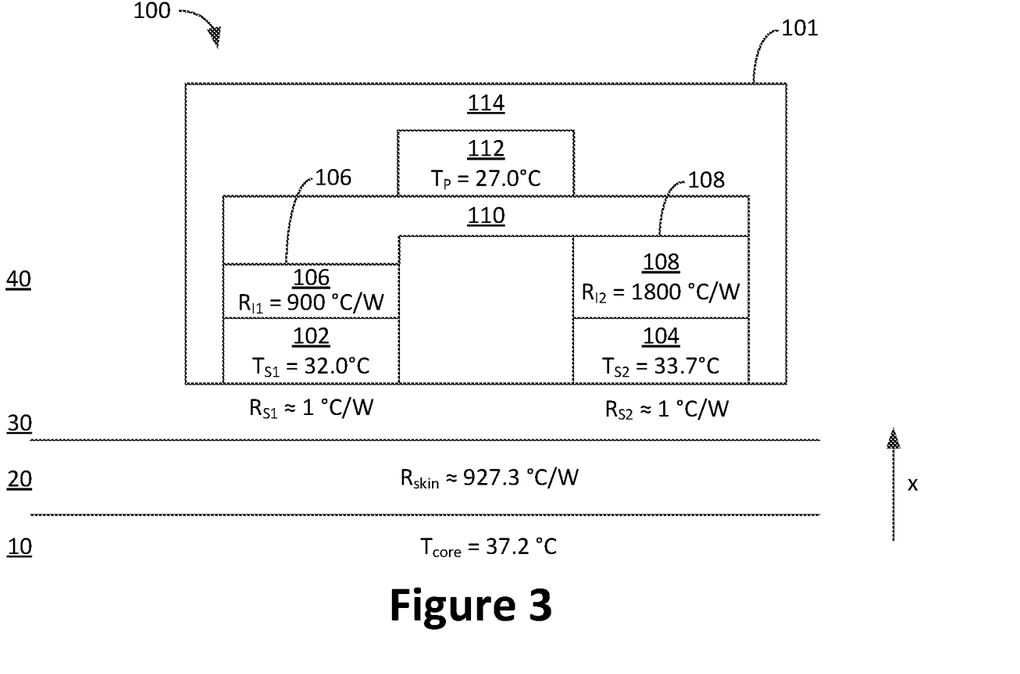
FIG. 3 illustrates example values for data associated with the example measurement device of FIG. 1, according to aspects of the present disclosure.

FIG. 3 shows example values for the temperatures $T_{S1}$, $T_{S2}$, and $T_P$ as well as the thermal resistances $R_{I1}$ and $R_{I2}$. Using these values, the two equations (10) and (11) can be solved to find that the thermal resistance $R_{Skin+S1}$ equals 927.3° C./W and the core body temperature $T_{Core}$ equals 37.2° C.

In the foregoing calculations, the core body temperature $T_{Core}$ can be measured with greater accuracy by employing a first insulation material 106 with a thermal resistance $R_{I1}$ that is significantly different from the thermal resistance $R_{I2}$ of the second insulation material 108. For instance, in the example of FIG. 3, the thermal resistance $R_{I1}$ is 900° C./W and the thermal resistance $R_{I2}$ is 1800° C./W.

Additionally, although the thermal resistance $R_{S1}$, $R_{S2}$ associated with each temperature sensor 102, 104 may not be completely controllable, the thermal resistance $R_{S1}$, $R_{S2}$ is lower than the thermal resistance $R_{Skin}$. In the example of FIG. 3, for instance, the thermal resistances $R_{S1}$, $R_{S2}$ are on the order of 1.0° C./W. As such, the thermal resistance $R_{Skin}$ may be substantially equal to the thermal resistance $R_{Skin+S1}$ calculated above. Thus, in FIG. 3, the thermal resistance $R_{Skin}$ is substantially equal to 927.3° C./W.

Figure 4:
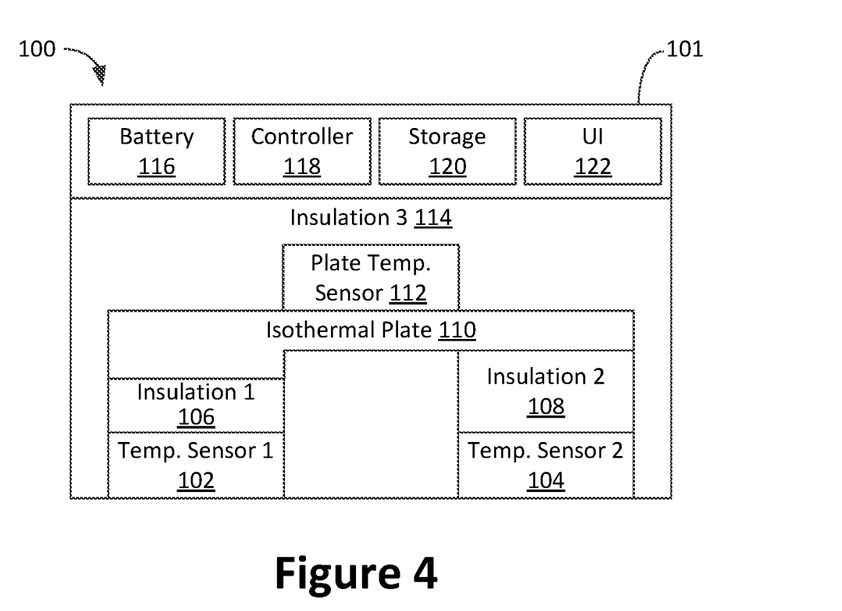
FIG. 4 illustrates additional components for the example measurement device of FIG. 1, according to aspects of the present disclosure.

As shown in FIG. 4, the measurement device 100 may also include a power source 116, a controller 118, a storage device 120, and a user interface 122. The components 116, 118, 120, 122 may be contained on board the measurement device 100 within the housing 101 as FIG. 4 illustrates. In alternative embodiments, however, the measurement device 100 may be coupled to an external power source, an external controller, an external storage device, and/or an external user interface in a larger system.

Figure 5:
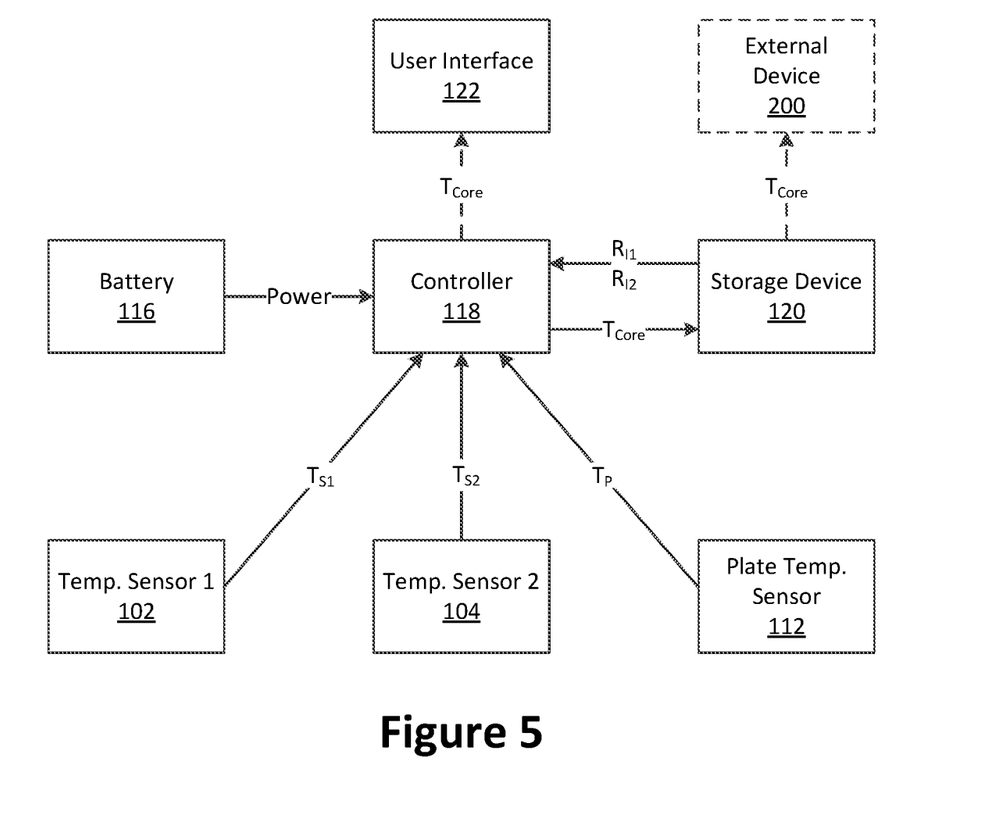
FIG. 5 illustrates an example exchange of data between components of the example measurement device of FIG. 1, according to aspects of the present disclosure.

As described above, the temperature sensors 102, 104, 112 may include thermistors, whose temperature-dependent resistance can be electrically determined to measure temperature. Accordingly, as shown in FIG. 4, the power source 116 can provide power to the controller 118. The controller 118 is coupled to each of the thermistors of the temperature sensors 102, 104, 112 by respective electrical circuits. By delivering a current to each thermistor and measuring a corresponding voltage drop, the controller 118 can determine the resistance of the thermistor and correlate the resistance to a temperature. In this way, as illustrated in FIG. 5, the temperature sensors 102, 104, 112 provide an electrical signal that allows the controller 118 to determine the temperatures $T_{S1}$, $T_{S2}$, $T_P$ measured by the temperature sensors 102, 104, and 112.

The storage device 120 may also store data relating to the known thermal resistance $R_{I1}$ for the first insulation material 106 and the known thermal resistance $R_{I2}$ for the second insulation material 108. As shown in FIG. 5, the controller 118 can retrieve the data relating to the thermal resistances $R_{I1}$ and $R_{I2}$ from the storage device 120, and with the temperatures $T_{S1}$, $T_{S2}$, $T_P$, the controller 118 can then calculate the core body temperature $T_{Core}$. The storage device 120 can be used to store the calculated core body temperature $T_{Core}$.

The user interface 122 can, alternatively or additionally, present the core body temperature $T_{Core}$ on a display, for instance. The user interface 122 may also provide other input devices, e.g., buttons, switches, etc., for controlling aspects of the measurement device 100.

Figure 9:
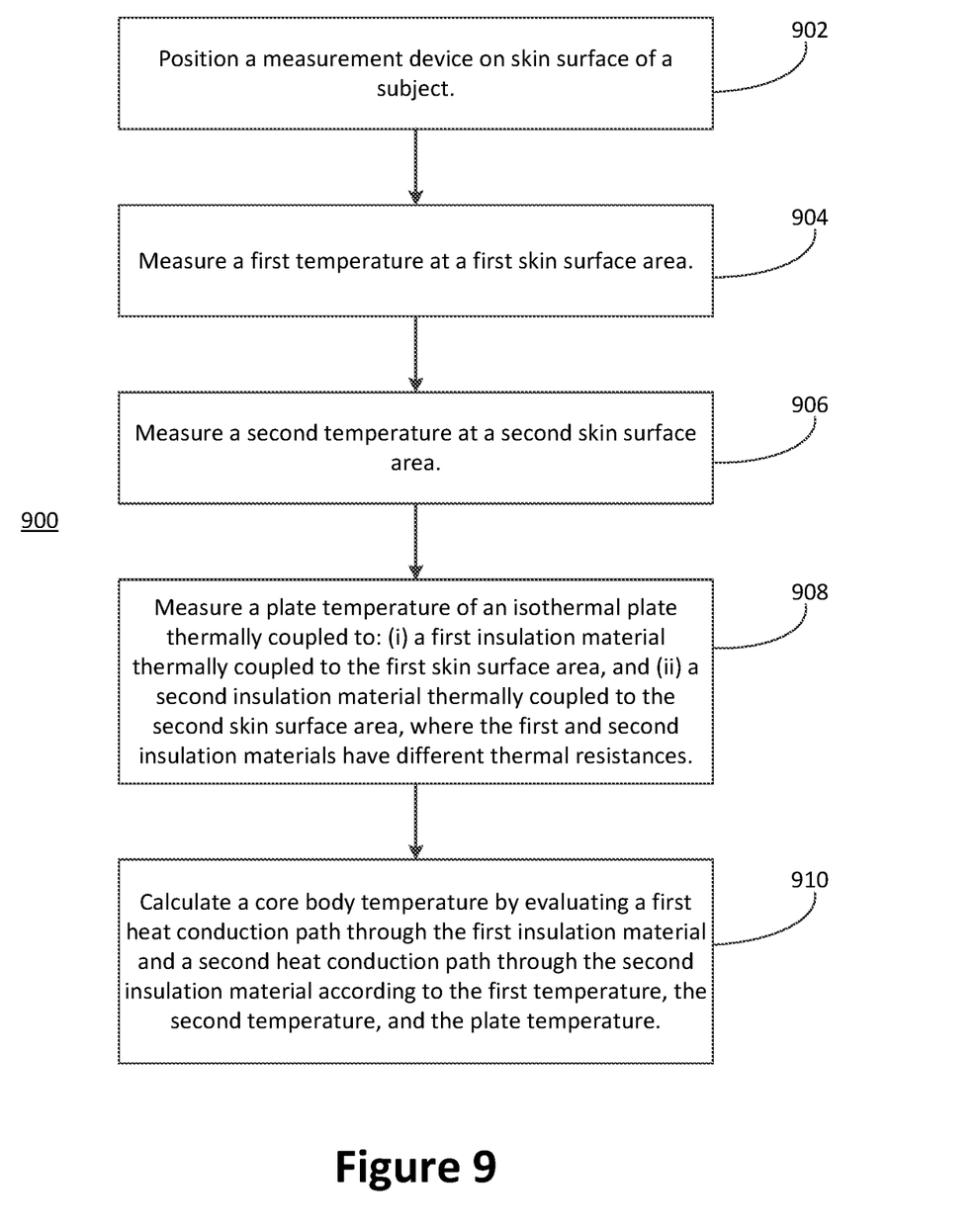
FIG. 9 illustrates an example approach for determining core body temperature, according to aspects of the present disclosure.

Accordingly, FIG. 9 illustrates an example approach 900 for determining a core body temperature of a person. In step 902, the measurement device 100 is positioned on a skin surface of a person. For instance, the first temperature sensor 102 is positioned at the first skin surface area 30a of a person. The first insulation material 106 is thermally coupled to the first skin surface area 30a, where the first insulation material 106 has the first thermal resistance $R_{I1}$. The second temperature sensor 104 is positioned at the second skin surface area 30b of the person, where the second temperature sensor 104 is spaced from the first temperature sensor 102. The second insulation material 108 is thermally coupled to the second skin surface area 30b. The second insulation material 108 has a second thermal resistance $R_{I2}$ that is different from the first thermal resistance $R_{I1}$. The isothermal plate 110 is thermally coupled to the first insulation material 102 and the second insulation material 104. The plate temperature sensor 112 is configured to measure a plate temperature $T_P$ of the isothermal plate 110. The core 10 of the person conducts heat along a first heat conduction path through the skin 20, the first insulation material 106, and the isothermal plate 110. The core 10 of the person conducts heat along a second heat conduction path through the skin 20, the second insulation material 108, and the isothermal plate 110.

In step 904, the first temperature $T_{S1}$ is measured at the first skin surface area 30a by the first temperature sensor 102. In step 906, the second temperature $T_{S2}$ is measured at the second skin surface area 30b by the second temperature sensor 104. In step 908, the plate temperature $T_P$ of the isothermal plate 110 is measured with the plate temperature sensor 112. In step 910, a core body temperature $T_{Core}$ is calculated by evaluating the first heat conduction path and the second heat conduction path based on the first temperature $T_{S1}$, the second temperature $T_{S2}$, the plate temperature $T_P$, the first thermal resistance $R_{I1}$, and the second thermal resistance $R_{I2}$.

According to some implementations, the measurement device 100 may be employed to collect periodic measurements of the core body temperature $T_{Core}$ over an extended period of time. The storage device 120 can store the plurality of measurements as they are collected. In some cases, the measurements can be stored with a date/time stamp and/or other identifying information. The measurements can be subsequently reviewed on a display/user interface on the measurement device 100. Alternatively or additionally, the measurements can be subsequently downloaded from the storage device 120 to another external device 200 as shown in FIG. 5, such as a computer, for further evaluation.

Advantageously, the measurement device 100 has relatively low power requirements for operation. The measurement device 100 uses power primarily to allow the controller 118 to: (i) send a current to each temperature sensor 102, 104, 112 in order to determine the temperatures $T_{S1}$, $T_{S2}$, and $T_P$, and (ii) calculate the core body temperature $T_{Core}$ from the temperatures $T_{S1}$, $T_{S2}$, and $T_P$. As such, the power source 116 may be a small, lightweight battery, e.g., a watch battery. Such a battery can provide the measurement device 100 with sufficient power to collect core body temperature data periodically over an extended period of time. Because the power source 116 can be small and lightweight, the measurement device 100 can have a small form factor that can be conveniently and easily worn by a person over an extended period of time. In contrast, other temperature measurement devices, such as those employing heating elements, cannot have a similar form factor because they require more power than can be provided by an on-board battery.

Figure 6A:
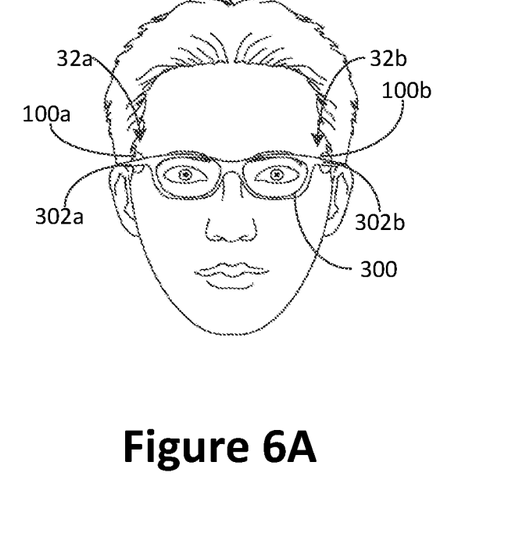
FIGS. 6A-D illustrate example implementations for a measurement device that determines core body temperature, according to aspects of the present disclosure.

FIGS. 6A-D illustrate example implementations for the measurement device 100. As shown in FIG. 6A, two measurement devices 100a, b may be combined with a frame 300 for eyeglasses. In particular, the measurement devices 100a, b can be securely coupled to respective temples 302a, b of the frame 300 using fasteners, adhesive, tape, hook-and-loop fasteners, elastic bands, and/or the like. The measurement devices 100a, b are sufficiently small and lightweight so that the person can wear the frame 300 comfortably. The measurement devices 100 are positioned so that they can make full and consistent contact with skin surface areas 32a and 32b corresponding to the temples of the person's head, where the core body temperature $T_{Core}$ can be measured from the temporal arteries as described above. Advantageously, the measurement devices 100a, b provide two independent measurements of the core body temperature $T_{Core}$, which can be compared and/or averaged to help promote accuracy.

Figure 6B:
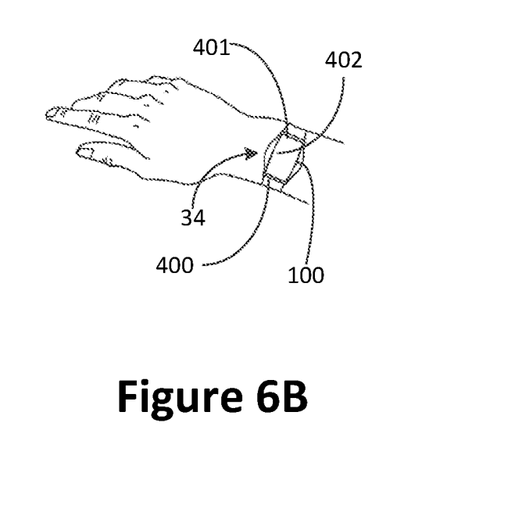

In another implementation, the measurement device 100 may be combined with a wrist device 400, such as a watch or fitness band. The measurement device 100 may be integral with the wrist device 400, where a housing 401 of the wrist device 400 also houses the components of the measurement device 100. Additionally, the user interface 402 for the wrist device 400 can also act as the user interface 122 for the measurement device 100. If the wrist device 400 is a fitness band, for example, the core body temperature $T_{Core}$ can be displayed with other types of fitness data, such as heart rate, calories burned, etc. Furthermore, a battery for the wrist device 400 can power the measurement device 100. Alternatively, the measurement device 100 may be coupled as a physically separate device to the back of the wrist device 400. The wrist device 400 positions the measurement device 100 so that it can take measurements of the core body temperature $T_{Core}$ from a skin surface area 34 on the person's wrist. The fit of the wrist device 500 can help press the measurement device 100 against the skin surface area 24 to achieve full and consistent contact.

In general, one or more of the measurement devices 100 may be combined with any type of wearable devices. In another example, for instance, the measurement device 100 may be combined with headphones.

Figure 6C:
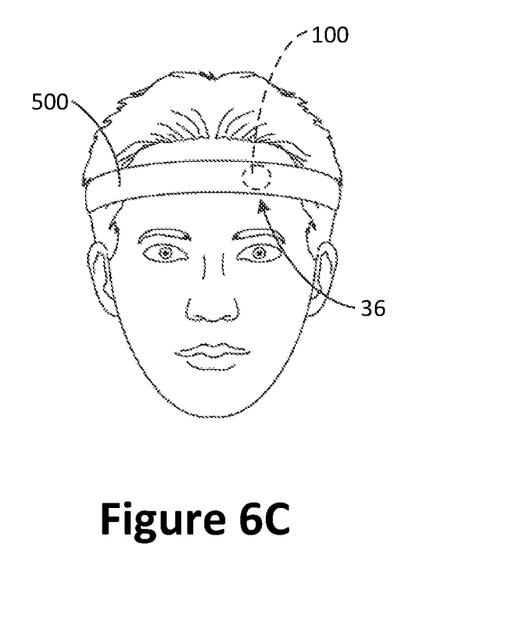
Figure 6D:
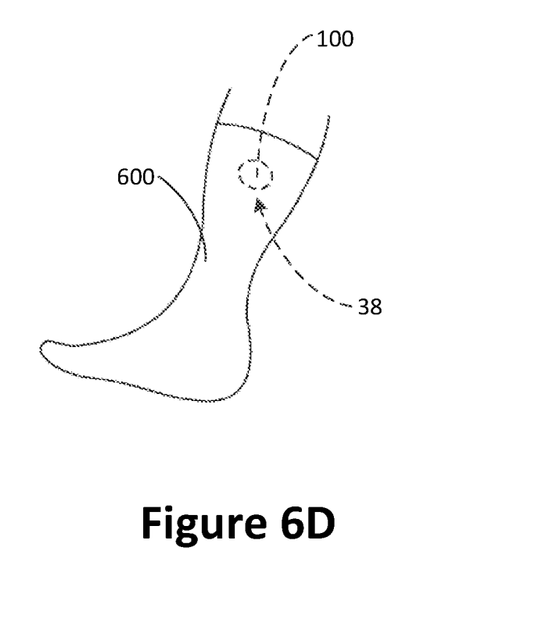

As shown in FIGS. 6C-D, at least one measurement device 100 may be combined with a wearable garment. For instance, as FIG. 6C illustrates, the measurement device 100 may be sewn into a headband 500 and/or otherwise coupled to the headband 500 by fasteners, adhesives, tape, hook-and-loop fasteners, and/or the like. The measurement device 100 is positioned so that it can take measurements of the core body temperature $T_{Core}$ from a skin surface area 36 on the person's forehead or temple. The tight fit of the headband 500 can help press the measurement device 100 against the skin surface area 36 to achieve full and consistent contact.

As shown in FIG. 6D, at least one measurement device 100 is combined with a sock 600 that is worn about the person's foot and ankle. The measurement device 100 may be sewn into the sock 600 and/or otherwise coupled to the sock 600 by fasteners, adhesives, tape, hook-and-loop fasteners, and/or the like. The measurement device 100 is positioned so that it can take measurements of the core body temperature $T_{Core}$ from a skin surface area 38 near the person's ankle or foot. The tight fit of the sock 600 can help press the measurement device 100 against the skin surface area to achieve full and consistent contact.

In general, one or more of the measurement devices 100 may be combined with any type of clothing, also including, but not limited to, hats, gloves, shoes, undergarments, etc. As with the headband 400 and the sock 500, these other types of clothing can position the one or more measurement devices 100 on skin surface areas to measure the core body temperature $T_{Core}$ as described above.

Although the embodiments above may analyze heat conduction along two conduction paths passing through the two skin surface areas 30a, b to calculate the core body temperature $T_{Core}$, other embodiments may analyze more than two conduction paths passing through more than two respective skin surface areas. The analysis of additional conduction paths can improve the accuracy of the calculation of the core body temperature $T_{Core}$.

Figure 7:
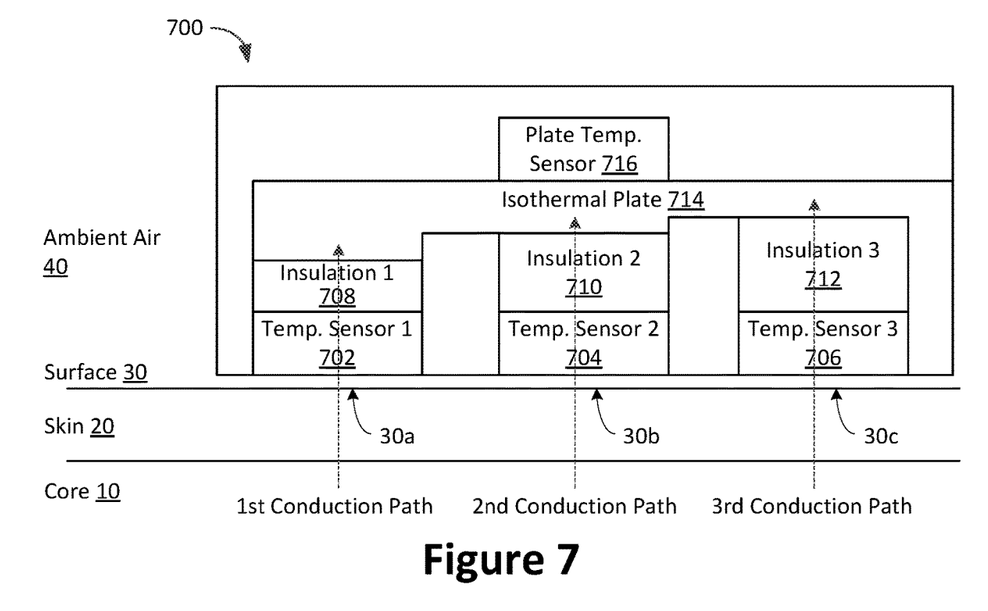
FIG. 7 illustrates another example measurement device that determines core body temperature, according to aspects of the present disclosure.

FIG. 7, for instance, illustrates another example measurement device 700 that includes a first temperature sensor 702, a second temperature sensor 704, and a third temperature sensor 706 that measure temperatures $T_{S1}$, $T_{S2}$, $T_{S3}$ at respective skin surface areas 30a, b, c. In addition, the measurement device 700 includes a first insulation material 708, a second insulation material 710, and a third insulation material 712 with different respective thermal resistances. Furthermore, the measurement device 700 includes an isothermal plate 714 and a corresponding plate temperature sensor 716 than measures a temperature $T_P$ of the isothermal plate 714.

Heat is conducted from the core 10 and through the skin 20 along three conduction paths. The first heat conduction path includes the first temperature sensor 702, the first insulation material 708, and the isothermal plate 714. The second heat conduction path includes the second temperature sensor 704, the second insulation material 710, and the isothermal plate 714. The third heat conduction path includes the third temperature sensor 706, the third insulation material 712, and the isothermal plate 714. Analyzing the three heat conduction paths as described above allows the core body temperature $T_{Core}$ to be calculated accurately. For instance, a first measurement of the core body temperature $T_{Core}$ may be determined from the first and second conduction paths; a second measurement of the core body temperature $T_{Core}$ may be determined from the first and third conduction paths; and a third measurement of the core body temperature $T_{Core}$ may be determined from the second and third conduction paths. The first, second, and third conduction paths can be averaged or otherwise evaluated to determine a more accurate calculation for the core body temperature $T_{Core}$.

Figure 8:
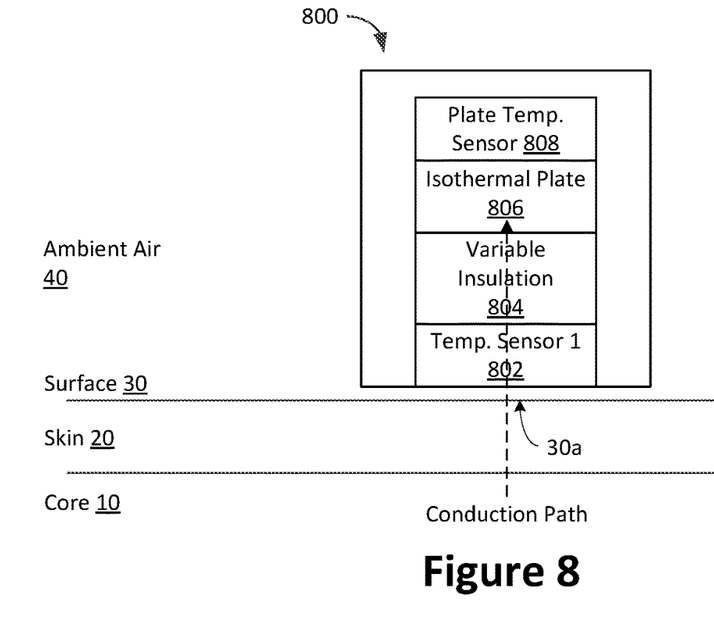
FIG. 8 illustrates yet another example measurement device that determines core body temperature, according to aspects of the present disclosure.

Each heat conduction path in the embodiments above may employ respective insulation materials with a predetermined thermal resistance, e.g., the first insulation material 106 with a thermal resistance $R_{I1}$ and the second insulation material 108 with a thermal resistance $R_{I2}$ for measurement device 100. Other embodiments, however, may employ a single conduction path with an insulation material that has a variable thermal resistance. As shown in FIG. 8, for instance, a measurement device 800 includes a temperature sensor 802 and an insulation material 804. The insulation material 804 has an electronically adjustable thermal resistance. The measurement device 100 also includes an isothermal plate 806 and a corresponding temperature sensor 808 that measures the temperature of the isothermal plate 806.

Heat is conducted from the core 10 and through the skin 20 along a conduction path that is defined by the temperature sensor 802, the insulation material 804, and the isothermal plate 806. The temperature sensor 802 can measure a temperature at a skin surface area 30a. Because the insulation material 804 has a variable thermal resistance, the measurement device 800 does not take temperature measurements from another skin surface area. Rather, the measurement device 800 can control the insulation material 804 to have a first thermal resistance of $R_{f1}$ and take corresponding measurements of: (i) a temperature $T_{S1A}$ of the skin surface 30a with the temperature sensor 802, and (ii) a temperature $T_{PA}$ with the temperature sensor 808. Subsequently, the measurement device 800 can modify the insulation material 804 to have a second thermal resistance of $R_{f2}$ and take corresponding measurements of: (i) a temperature $T_{S1B}$ at the same skin surface area 30a with the temperature sensor 802, and (ii) a temperature $T_{PB}$ of the isothermal plate 806 with the temperature sensor 808. The two sets of measurements effectively provide two conduction paths, which can be analyzed to calculate the core body temperature $T_{Core}$ in a manner similar to that described above.

In some cases, the measurement device 800 may modify the insulation material 804 more than once to obtain more than two sets of measurements that effectively provide more than two conduction paths. For instance, if the insulation material 804 is modified to have a third thermal resistance of $R_{f3}$, the measurement device 800 can take measurements of: (i) a temperature $T_{S1C}$ at the same skin surface area 30a with the temperature sensor 802, and (ii) a temperature $T_{PC}$ of the isothermal plate 806 with the temperature sensor 808. A first measurement of the core body temperature $T_{Core}$ may be determined from the first and second sets of measurements; a second measurement of the core body temperature $T_{Core}$ may be determined from the first and third sets of measurements; and a third measurement of the core body temperature $T_{Core}$ may be determined from the second and third sets of measurements. The first, second, and third measurements of the core body temperature $T_{Core}$ can be averaged or otherwise evaluated to determine a more accurate calculation for the core body temperature $T_{Core}$.

Although each measurement device in the embodiments above may employ one isothermal plate, other embodiments may employ more than one isothermal plate. For instance, the insulation material in each heat conduction path may be coupled to a separate isothermal plate, where each isothermal plate has a corresponding temperature sensor.

Although the temperature sensors in the embodiments above may employ thermistors, other embodiments are not limited to the use of thermistors. For instance, temperature sensors may include thermocouples, resistive temperature detectors (RTDs), and/or other types of measurement devices.

IV. CONCLUSION

In view of the foregoing, example temperature measurement systems determine core body temperature accurately from temperature measurements taken at the skin surface by accounting for the thermal resistance of the skin on the temperature measurements. To determine the thermal resistance of the skin, the example temperature measurement systems evaluate how heat from the core of the body is conducted through the skin in response to varying thermal resistance loads. Advantageously, the example embodiments have low power requirements, allowing the example temperature measurements to have a small form factor that can be easily and conveniently worn by a person to collect core body temperature measurements over an extended period of time.

The embodiments described herein employ devices for processing information and controlling aspects of the example systems, e.g., the controller 118. Such devices may be implemented as a combination of hardware and software elements. The hardware elements may include combinations of operatively coupled hardware components, including microprocessors, memory, signal filters, circuitry, etc. The processors may be configured to perform operations specified by the software elements, e.g., computer-executable code stored on computer readable medium. The processors may be implemented in any device, system, or subsystem to provide functionality and operation according to the present disclosure. The processors may be implemented in any number of physical devices/machines. Indeed, parts of the processing of the example embodiments can be distributed over any combination of processors for better performance, reliability, cost, etc.

The physical devices/machines can be implemented by the preparation of integrated circuits or by interconnecting an appropriate network of conventional component circuits, as is appreciated by those skilled in the electrical art(s). The physical devices/machines, for example, may include field programmable gate arrays (FPGA's), application-specific integrated circuits (ASIC's), digital signal processors (DSP's), etc.

Appropriate software can be readily prepared by programmers of ordinary skill based on the teachings of the example embodiments, as is appreciated by those skilled in the software arts. Thus, the example embodiments are not limited to any specific combination of hardware circuitry and/or software. Stored on one computer readable medium or a combination of computer readable media, the computing systems may include software for controlling the devices and subsystems of the example embodiments, for driving the devices and subsystems of the example embodiments, for enabling the devices and subsystems of the example embodiments to interact with a human user (user interfaces, displays, controls), etc. Such software can include, but is not limited to, device drivers, operating systems, development tools, applications software, etc. A computer readable medium further can include the computer program product(s) for performing all or a portion of the processing performed by the example embodiments. Computer program products employed by the example embodiments can include any suitable interpretable or executable code mechanism, including but not limited to complete executable programs, interpretable programs, scripts, dynamic link libraries (DLLs), applets, etc. The processors may include, or be otherwise combined with, computer-readable media. Some forms of computer-readable media may include, for example, a hard disk, any other suitable magnetic medium, any suitable optical medium, RAM, PROM, EPROM, flash memory, any other suitable memory chip or cartridge, any other suitable non-volatile memory, a carrier wave, or any other suitable medium from which a computer can read.

The processing/control devices may also include databases for storing data. Such databases may be stored on the computer readable media described above and may organize the data according to any appropriate approach. For examples, the data may be stored in relational databases, navigational databases, flat files, lookup tables, etc.

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A temperature measurement system for determining a body temperature of a person, comprising:
   a first temperature sensor;
   a first insulation material thermally coupled to the first temperature sensor and having a first thermal resistance;
   a second temperature sensor spaced apart from the first temperature sensor;
   a second insulation material spaced apart from the first insulation material, the second insulation material thermally coupled to the second temperature sensor and having a second thermal resistance that is different from the first thermal resistance;
   an isothermal plate thermally coupled to the first insulation material and the second insulation material, the first insulation material disposed between the first temperature sensor and the isothermal plate, and the second insulation material disposed between the second temperature sensor and the isothermal plate;
   an isothermal plate temperature sensor thermally coupled to the isothermal plate,
      wherein the first insulation material is configured to provide a first heat conduction along a first heat conduction path to the isothermal plate, and the first temperature sensor is configured to correspondingly measure a first temperature associated with the first heat conduction, and
      the second insulation material is configured to provide a second heat conduction along a second heat conduction path to the isothermal plate, and the second temperature sensor is configured to correspondingly measure a second temperature associated with the second heat conduction; and
   a controller electrically coupled to the first temperature sensor, the second temperature sensor, and the isothermal plate temperature sensor, the controller calculating a body temperature by solving:

$$T_{Core}=[((R_{Skin+S1}+R_{I1})/R_{I1})*(T_{S1}-T_P)]+T_P$$

$$T_{Core}=[((R_{Skin+S1}+R_{I2})/R_{I2})*(T_{S2}-T_P)]+T_P$$

for $T_{Core}$, where $T_{Core}$ is the body temperature, $R_{I1}$ is the first thermal resistance, $R_{I2}$ is the second thermal resistance, $T_{S1}$ is the first temperature, $T_{S1}$ is the second temperature, $T_P$ is an isothermal plate temperature measured by the isothermal plate temperature sensor, and $R_{Skin+S1}$ is a thermal resistance associated with the first temperature sensor and a skin of the body.

2. The measurement system of claim 1, further comprising a battery electrically coupled to the controller.

3. The measurement system of claim 2, further comprising a housing containing the first temperature sensor, the second temperature sensor, the isothermal plate temperature sensor, the first insulation material, the second insulation material, the isothermal plate, the controller, and the battery.

4. The measurement system of claim 3, further comprising a wearable device or garment coupled to the housing.

5. The measurement system of claim 1, further comprising:
   a third temperature sensor; and
   a third insulation material thermally coupled to the third temperature sensor and having a third thermal resistance that is different from the first thermal resistance and the second thermal resistance,
   wherein the isothermal plate is further thermally coupled to the third insulation material,
   the third insulation material is configured to provide a third heat conduction along a third heat conduction path and to the isothermal plate, the third temperature sensor correspondingly measuring a third temperature associated with the third heat conduction, and
   the controller further calculates an additional measurement of the body temperature by solving:

$$T_{Core}'=[((R_{Skin+S1}+R_{I1})/R_{I1})*(T_{S1}-T_P)]+T_P$$

$$T_{Core}'=[((R_{Skin+S1}+R_{I3})/R_{I3})*(T_{S1}-T_P)]+T_P$$

for $T_{Core}'$, where $T_{Core}'$ is the additional measurement of the body temperature, $R_{I1}$ is the first thermal resistance, $R_{I3}$ is the third thermal resistance, $T_{S1}$ is the first temperature, $T_{S3}$ is the third temperature, $T_P$ is the isothermal plate temperature, and $R_{Skin+S1}$ is the thermal resistance associated with the first temperature sensor and the skin of the body.

6. The measurement system of claim 1, further comprising a third insulation material that insulates the first temperature sensor, the second temperature sensor, the isothermal plate temperature sensor, the first insulation material, the second insulation material, and the isothermal plate from ambient air.

7. The measurement system of claim 1, wherein the first temperature sensor, the second temperature sensor, and the isothermal plate temperature sensor include thermistors.

8. A method for determining a body temperature of a person, comprising:

positioning a measurement device on a skin surface of a person, the measurement device including:
a first temperature sensor;
a first insulation material thermally coupled to the first temperature sensor and having a first thermal resistance;
a second temperature sensor spaced apart from the first temperature sensor;
a second insulation material thermally coupled to the second temperature sensor and having a second thermal resistance that is different from the first thermal resistance;
an isothermal plate thermally coupled to the first insulation material and the second insulation material; and
an isothermal plate temperature sensor thermally coupled to the isothermal plate,
wherein the first insulation material is configured to provide a first heat conduction along a first heat conduction path from the body of the person and to the isothermal plate, and the second insulation material is configured to provide a second heat conduction along a second heat conduction path from the body of the person- and to the isothermal plate;
measuring, with the first temperature sensor, a first temperature associated with the first heat conduction;
measuring, with the second temperature sensor, a second temperature associated with the second heat conduction;
measuring, with the isothermal plate temperature sensor, an isothermal plate temperature of the isothermal plate; and
calculating, with a controller, a body temperature of the body of the person by solving:

$$T_{Core}=[((R_{Skin+S1}+R_{I1})/R_{I1})*(T_{S1}-T_P)]+T_P$$

$$T_{Core}=[((R_{Skin+S1}+R_{I2})/R_{I2})*(T_{S2}-T_P)]+T_P$$

for $T_{Core}$, where $T_{Core}$ is the body temperature, $R_{I1}$ is the first thermal resistance, $R_{I2}$ is the second thermal resistance, $T_{S1}$ is the first temperature, $T_{S2}$ is the second temperature, $T_P$ is the isothermal plate temperature, and $R_{Skin+S1}$ is a thermal resistance associated with the first temperature sensor and a skin of the body.

9. The method of claim 8, wherein the controller is electrically coupled to the first temperature sensor, the second temperature sensor, and the isothermal plate temperature sensor, and the controller controls measuring the first temperature, the second temperature, and the isothermal plate temperature with the first temperature sensor, the second temperature sensor, and the isothermal plate temperature sensor, respectively.

10. The method of claim 9, further comprising delivering power to the controller with a battery.

11. The method of claim 10, wherein positioning a measurement device on the skin surface includes positioning a housing of the measurement device on the skin surface, the housing containing the first temperature sensor, the second temperature sensor, the isothermal plate temperature sensor, the first insulation material, the second insulation material, the isothermal plate, the controller, and the battery.

12. The method of claim 11, wherein positioning a measurement device on the skin surface includes positioning a wearable device or garment on the person, the measurement device being coupled to the wearable device or garment.

13. The method of claim 8, wherein the measurement device includes:

a third temperature sensor; and
a third insulation material thermally coupled to the third temperature sensor and having a third thermal resistance that is different from the first thermal resistance and the second thermal resistance,
wherein the isothermal plate is further thermally coupled to the third insulation material, and
the third insulation material is configured to provide a third heat conduction along a third heat conduction path from the body of the person and to the isothermal plate, and the third temperature sensor is configured to correspondingly measure a third temperature associated with the third heat conduction, and
the method further comprises calculating, with the controller, an additional measurement of the body temperature by solving:

$$T_{Core}'=[((R_{Skin+S1}+R_{I1})/R_{I1})*(T_{S1}-T_P)]+T_P$$

$$T_{Core}'=[((R_{Skin+S1}+R_{I3})/R_{I3})*(T_{S3}-T_P)]+T_P$$

for $T_{Core}'$, where $T_{Core}'$ is the additional measurement of the body temperature, $R_{I1}$ is the first thermal resistance, $R_{I3}$ is the third thermal resistance, $T_{S1}$ is the first temperature, $T_{S3}$ is the third temperature, $T_P$ is the isothermal plate temperature, and $R_{Skin+S1}$ is the thermal resistance associated with the first temperature sensor and the skin of the body.

14. A temperature measurement system for determining a body temperature of a person, comprising:
a plurality of skin surface temperature sensors,
a plurality of insulation materials thermally coupled respectively to the plurality of skin surface temperature sensors, the insulation materials having different respective thermal resistances;
an isothermal plate thermally coupled to the plurality of insulation materials;
an isothermal plate temperature sensor in thermal contact with the isothermal plate and measuring an isothermal plate temperature for the isothermal plate; and
a controller electrically coupled to the plurality of skin surface temperature sensors and the isothermal plate temperature sensor to determine respective skin surface temperatures and the isothermal plate temperature, the controller calculating a body temperature from a body of the person by evaluating heat conduction paths from the body of the person, through the plurality of insulation materials, and to the isothermal plate, wherein each heat conduction is evaluated at least according to a heat transfer based on a temperature difference between the isothermal plate temperature and the skin surface temperature measured by the corresponding skin surface temperature sensor in the heat conduction path, and dividing the temperature difference by the corresponding thermal resistance of the insulation material in the heat conduction path.

15. The measurement system of claim 14, further comprising a battery coupled to the controller.

16. The measurement system of claim 15, further comprising a housing containing the plurality of skin surface temperature sensors, the plurality of insulation materials, the isothermal plate, the isothermal plate temperature sensor, the controller, and the battery.

17. The measurement system of claim 16, further comprising a wearable device or garment coupled to the housing.

18. The measurement system of claim 14, further comprising an additional insulation material that insulates the skin surface temperature sensors, the plurality of insulation materials, the isothermal plate, and the isothermal plate temperature sensor from ambient air.

19. The measurement system of claim 14, wherein the plurality of skin surface temperature sensors and the isothermal plate temperature sensor include thermistors.

* * * * *